United States Patent [19]

Sperry, III et al.

[11] 4,375,170

[45] Mar. 1, 1983

[54] DECONTAMINATING FLUID SENSOR MECHANISM

[75] Inventors: Elmer A. Sperry, III, Pompton Plains; Robert F. Legenhausen, Bound Brook, both of N.J.

[73] Assignee: Beckman Instruments, Inc., Fullerton, Calif.

[21] Appl. No.: 248,612

[22] Filed: Mar. 27, 1981

[51] Int. Cl.³ .............................................. G01N 1/22
[52] U.S. Cl. .................................. 73/863.85; 73/432 R
[58] Field of Search ............ 73/863.85, 863.86, 863.81, 73/863.83, 863.84, 864.81, 432 B; 137/15, 237

[56] References Cited

U.S. PATENT DOCUMENTS

| | | | |
|---|---|---|---|
| 2,171,576 | 9/1939 | Larry et al. | 137/15 |
| 2,887,443 | 5/1959 | Blue et al. | 204/64 |
| 3,246,521 | 4/1966 | Humphrey | 73/374 |
| 4,096,754 | 6/1978 | Beveridge, Jr. et al. | 73/863.85 X |

FOREIGN PATENT DOCUMENTS 55-75618  6/1980  Japan .................................. 73/432 B Primary Examiner—Jerry W. Myracle
Attorney, Agent, or Firm—R. J. Steinmeyer; P. R. Harder; Edward C. Jason

[57] ABSTRACT

A sensor mechanism for measuring a property of a fluid which must not be allowed to escape into the environment. A sensor housing provides a chamber from which a sensing element may be extended into contact with the fluid to be measured, and into which the sensing element may be retracted prior to being sealed off from the fluid. When the sensing element is in its retracted position, the closure of a valve seals the chamber off from contact with the fluid. A purging inlet and a purging outlet allow the interior of the sensor housing to be purged of traces of fluid trapped therein by the closure of the valve, prior to the time that the sensor housing is disassembled for the servicing or replacement of the sensing element. An improved sealing arrangement allows the interior of the sensor housing to remain sealed off from the environment without the use of sliding seals. An improved cleaning arrangement allows the sensing element to be cleaned without removing it from the sensor housing.

23 Claims, 8 Drawing Figures

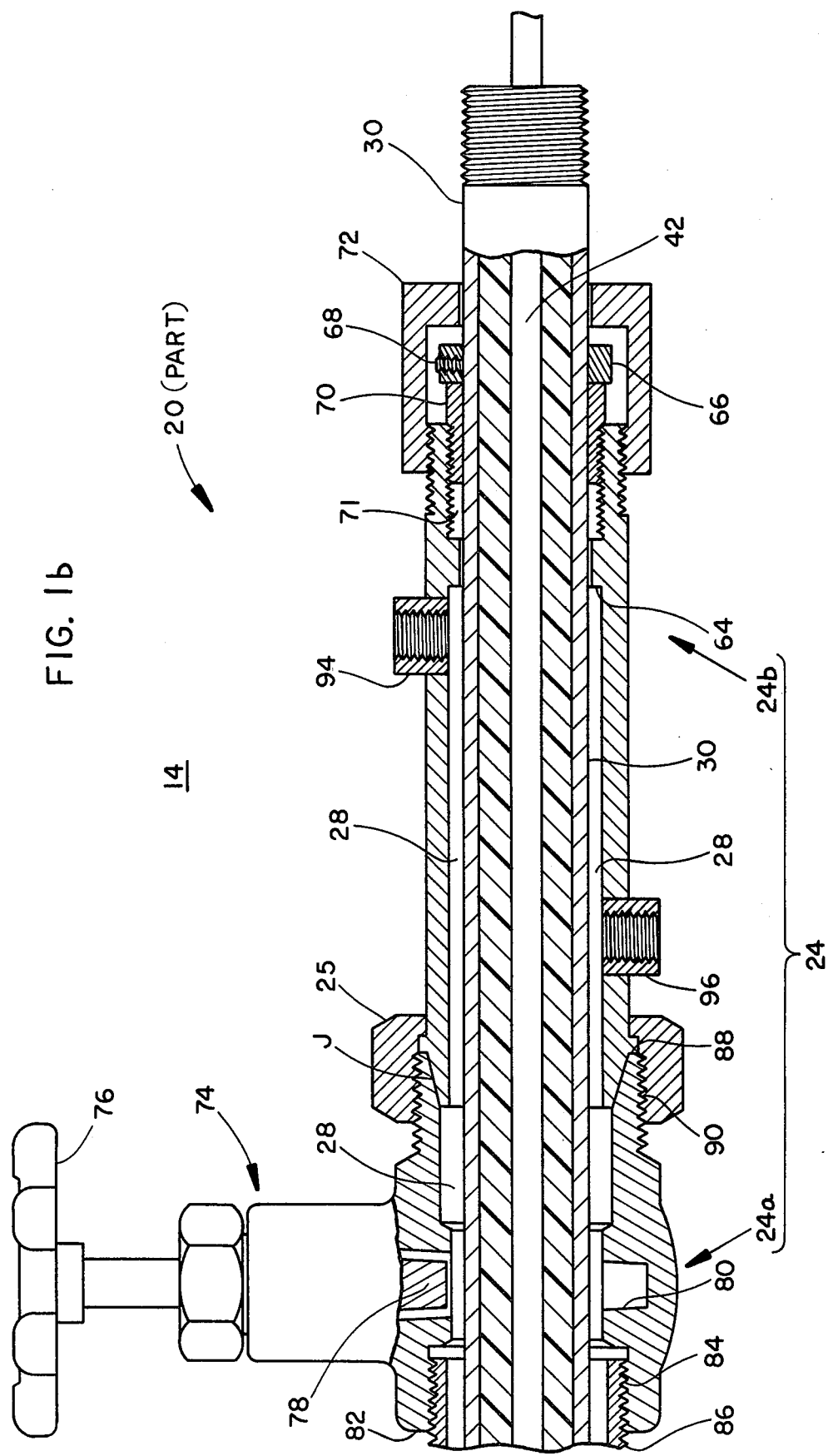

DECONTAMINATING FLUID SENSOR MECHANISM

BACKGROUND OF THE INVENTION

Under circumstances where measurements must be made on a fluid that is toxic or hazardous to human health, care must be exercised to prevent even small quantities of the fluid from escaping during the insertion, removal or replacement of a sensing element. In processes that use carcinogenic compounds, for example, the release of even tiny amounts of such compounds into the work environment during the course of the insertion and/or removal of a sensing element, such as a conductivity probe, can result in a significant long term health hazard for the workers who operate the process. The need for a more nearly completely leak-proof sensor mechanism of this type has become increasingly urgent as the list of compounds known to be hazardous to human health has grown with advances in medical knowledge.

One approach to solving this problem has involved the avoidance of direct contact between the sensing element and the sample fluid. An example of this approach is shown in U.S. Pat. No. 3,246,521 issued in the name of L. A. Humphrey on Apr. 19, 1966. In the referenced patent, the sensing element is a thermometer that is exposed to the sample fluid only through a protective jacket. When the thermometer is to be removed or replaced, the jacket is withdrawn into the interior of the sensor mechanism and sealed off from the environment by means of a suitable valve.

One disadvantage of the above described structure is that it provides no way of preventing the escape of the residual quantities of sample fluid that are trapped in the interior of the mechanism after the closure of the valve. Instead, the small interior volume of the mechanism is relied upon to assure that the amount of the sample fluid that escapes is small. Recent advances in medical science, however, indicate that even extremely small quantities of hazardous substances can, over a period of prolonged exposure, give rise to serious health problems. Thus, prior to the present invention, sensor mechanisms of the above type were not sufficiently effective in eliminating the problem of human exposure.

Another approach to dealing with the problem of preventing hazardous substances from entering the human environment is described in U.S. Pat. No. 2,887,443 issued in the name of R. D. Blue et al. on May 19, 1959. In devices of the latter type, an electrode used in an electrolytic cell is withdrawn from the contaminated interior atmosphere of the cell into a side chamber having sliding metal doors that are intended to close the chamber off from the electrolytic cell. The interior of the chamber is then purged by pumping clean air into the chamber while allowing the contaminating gas to escape through a purge outlet duct. The electrode was then removed by loosening the bolts that sealed the top plate of the side chamber to the body thereof.

One problem with the above described structure was that the abutting seal provided by the meeting of the sliding metal doors was only partly effective. Moreover, the seal between the sliding doors and the structure that supported them provided an additional avenue for escape of noxious gases. As a result, this structure provided protection only against the large scale escape of gas from the electrolytic cell.

Another shortcoming of the above-described structure is that the removal and replacement of the electrode element was a laborious process requiring the loosening and tightening of numerous bolts. In addition, the above structure has a number of sliding seals and gaskets the deterioration of which could result in further escape of noxious gases. This problem was especially severe because of the extremely high temperature and highly corrosive environment of the electrolytic cell.

SUMMARY OF THE INVENTION

In accordance with the present invention, the above-described problems are solved by providing a sensor mechanism having an improved sealing arrangement for preventing even small quantities of a fluid from escaping during the movement of a sensing element into and out of contact with a sample fluid. In addition, these problems are solved by providing a purging inlet and outlet whereby even the small interior space of the sensor mechanism may be purged of the sample fluid prior to being opened to the atmosphere for the servicing or replacement of the sensing element. As a result, the sensor mechanism of the present invention allows a sensing element to be inserted, retracted and replaced without the escape of any measurable quantity of the sample fluid into the environment.

In accordance with one feature of the present invention, there is provided an improved sealing arrangement whereby the use of sliding seals may be completely eliminated. In the preferred embodiment of this feature a solid, expandable enclosure is provided between the housing of the sensor and the sensing element, the ends of the enclosure being permanently sealed to the relatively movable members that are to be sealed to one another. In this embodiment the enclosure may be expanded or contracted in the manner of a bellows or accordion to provide both the desired relative movement and the desired leak-proof enclosure.

In accordance with another feature of the present invention, the sensor is provided with structures whereby fluids may be directed against the sensing element to dislodge and remove accumulated dirt therefrom. In the preferred embodiment this cleaning is accomplished by the same fluid and at the same time as the desired purging. This is accomplished by introducing the purging fluid through suitable fluid directing elements, such as spray nozzles, which direct the purging fluid against those portions of the sensing element where the accumulation of dirt is most objectionable. Alternatively, a cleaning fluid having a different composition than the purging fluid may be applied to the sensing element, through the same or different inlets and outlets, after the purging process has been completed.

In another embodiment of the present invention, the empty space between the sensing element and the sensor housing is provided with constrictions which direct the flow of purging and/or cleaning fluid over the surface of the sensing element. This directed flow serves generally the same function as the above mentioned fluid directing elements, but provides the desired purging cleaning action in a gentler manner and over larger areas of the sensing element.

Still other objects and features of the present invention will be apparent from the following detailed description and drawings in which

DESCRIPTION OF THE DRAWINGS

FIGS. 1a and 1b together comprise a cross-sectional view of a complete sensor mechanism constructed in accordance with the present invention.

DESCRIPTION OF THE PREFERRED EMBODIMENTS

Figure 1A:
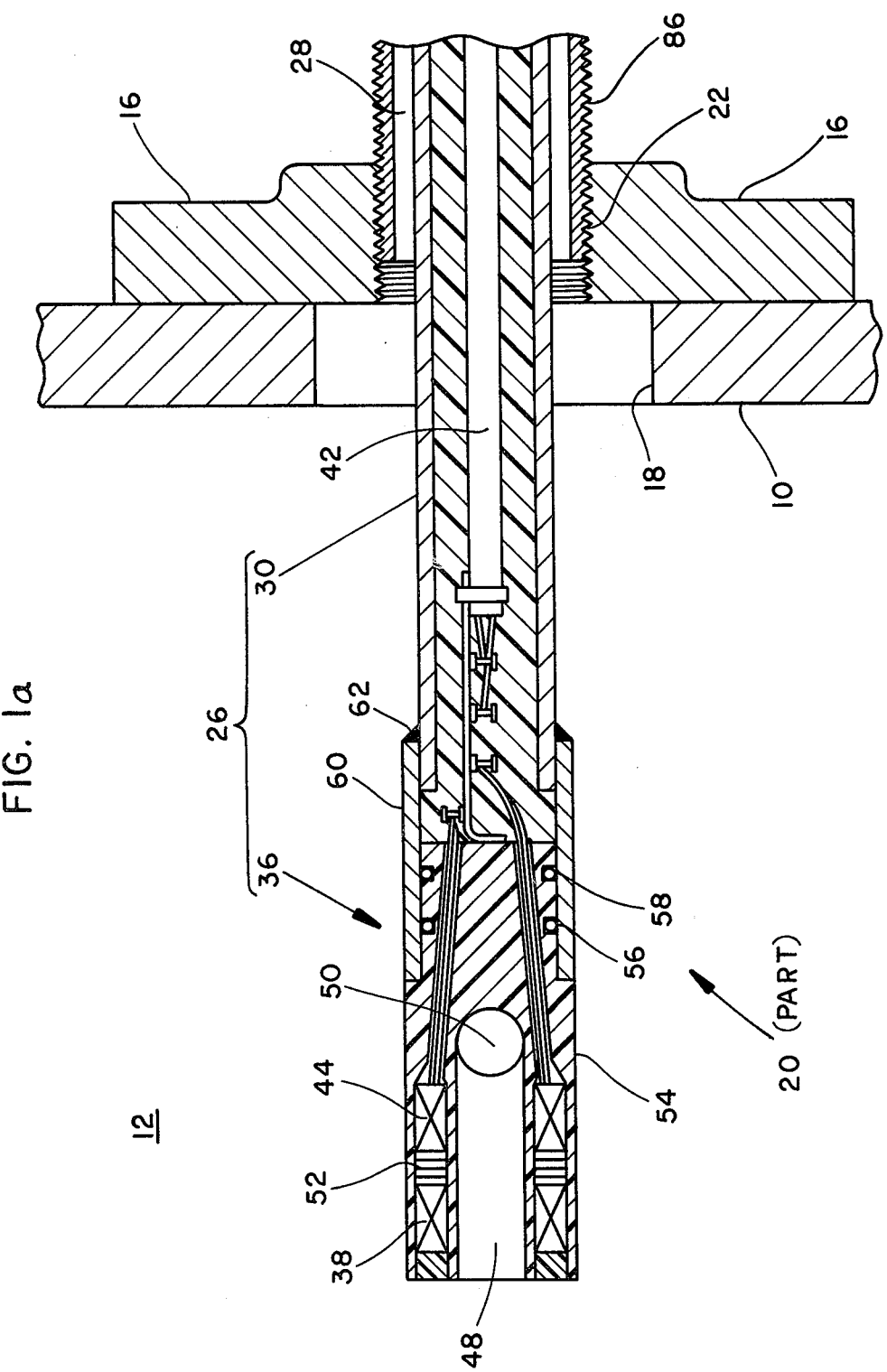

Referring to FIGS. 1a and 1b, there is shown in cross section a part of a retaining wall 10 which encloses a region 12 that contains a fluid substance, either a liquid or a gas, upon which measurements are to be made. Retaining wall 10 separates the fluid substance from the human environment, indicated generally by the designation 14. Region 12 might, for example, comprise the interior of a reaction vessel in which a batch of chemicals are mixed, or the interior of a pipe through which a fluid is transported between the stations of a continuous process.

Attached to retaining wall 10 is a mounting bracket or plate 16 for supporting a sensor mechanism 20 in the vicinity of an opening 18 in retaining wall 10. Mounting plate 16 is preferably permanently fastened to retaining wall 10 by, for example, welding. Sensor mechanism 20 is, in turn, mounted on mounting plate 16 by suitable threads 22. It will be understood that all of the joints between retaining wall 10, mounting plate 16 and sensor mechanism 20 are sufficiently leak-proof that none of the fluid in region 12 may escape into the human environment.

In the present embodiment sensor mechanism 20 includes a generally tubular housing 24 having a first section 24a and a second, detachable section 24b. These sections are joined end to end at a junction J. When these housing sections are fastened tightly together by a nut 25, junction J provides a leakproof seal therebetween. When, on the other hand, nut 25 is loosened, housing sections 24a and 24b may be separated to provide access to the interior of either housing section. The purpose of this access will be described more fully later.

Sensor mechanism 20 also includes a generally cylindrical sensing assembly 26 that is slidably mounted within and enclosed by housing 24. The space between housing 24 and sensing assembly 26 forms an internal chamber 28 within which assembly 26 may be moved in the axial direction with respect to housing 24. One end of chamber 28 is open to region 12 through opening 18; the other end of chamber 28 is closed to the atmosphere by means of the sliding seal provided by a bushing 71 that bridges the gap between housing 24 and sensing assembly 26. Thus, sensing assembly 26 may be extended into contact with the sample fluid or retracted entirely within chamber 28, without breaking the seal between regions 12 and 14.

Sensing assembly 26 includes a generally tubular mounting element 30 on the end of which is mounted a sensing element 36 which may be of any suitable type. Sensing element 36 may, for example, comprise a conductivity probe for measuring the electrical conductivity of the fluid in region 12. It will be understood, however, that sensing element 36 may measure any other property of interest such as temperature, pressure, etc.. For the sake of completeness, however, the structure of sensing element 36 and the manner in which the latter is connected to external circuitry through mounting element 30 will now be briefly described.

In the embodiment of FIG. 1, sensing element 36 is a transducer of the conductivity measuring type. More particularly, sensing element 36 includes an exciting coil 38 which is energized by a current that is supplied thereto through the conductors of a conductor bundle 42 that is located within mounting element 30. The conductivity of the fluid is measured by means of the induced current flowing through a pick-up coil 44, the leads of which are also routed through conductor bundle 42. Coils 38 and 44 surround a passage 48 that is open to the sample fluid in region 12. The free movement of this fluid is assured by providing, in sensing element 36, a through hole 50 which intersects passage 48, thereby providing a T-shaped internal passage for the sample fluid.

In order to prevent coils 38 and 44 from interacting magnetically, a metallic shield 52 is disposed therebetween. Coils 38 and 44 and shield 52 are preferably mounted in an insulating housing 54 of a material that does not react chemically with the sample fluid. Insulating housing 54 may, in turn, be attached to mounting element 30 by being press fit into a length of metal tube 60 that is welded to the end of mounting element 30. The compression for this fit may be provided by suitable O-rings 56 and 58. If desired to provide enhanced immunity from mechanical vibrations, the space between the interior of mounting element 30 and cable 42 may be filled with a suitable potting compound such as polyurethane foam.

At the opposite end of mounting element 30, conductor cable 42 may be extended until it reaches the main console of the conductivity measuring instrument (not shown) with which it operates. Preferably, however, both mounting element 30 and conductor cable 42 are terminated in a suitable junction box that contains a plug type connector that is wired to main console of the conductivity instrument. This arrangement provides a convenient way of coupling and uncoupling assembly 26 from an external instrument during the servicing of sensor mechanism 20. Because the junction box and connector are well known in the art they will not be shown or further described herein.

To the end that sensing assembly 26 may be removed from contact with the sample fluid, the diameter of chamber 28 is made large enough to allow sensing element 36 to be retracted or withdrawn into the interior thereof. This retracting movement may be continued until the increased diameter or stepped portion 60-62 of assembly 26 comes into contact with an internal shoulder or stop 64 of housing 24. Thus, shoulder 64 cooperates with the stepped diameter portion of assembly 26 to define a limit for the axial retracting movement of sensing element 36.

Conversely, if sensing assembly 26 is already in its retracted position, it may be extended into contact with the sample fluid by moving assembly 26 axially through hole 18. The limit for this axial extending movement is determined by the position of a stop ring 66 which is rigidly fastened to mounting element 30 by a set screw 68. Stop ring 66 limits the outward longitudinal motion of sensing assembly 26 by making contact with a threaded packing bushing 70 which is threaded into the interior surface of housing 24. In addition to limiting the outward movement of assembly 26, packing bushing 70 serves to compress sliding seal 71 to assure that a substantially leak-proof sliding seal exists between mounting element 30 and housing 24.

In addition to limiting the outward movement of sensing assembly 26, stop ring 66 cooperates with a knurled nut 72 to effectively lock sensing element 36 in its extended position. This occurs because knurled nut 72, like packing bushing 70, is fastened to housing 24. As a result, the freedom of movement of assembly 26 in its extended position is determined by the amount of space between the end of packing bushing 70 and the interior end of knurled nut 72.

In view of the foregoing, it will be seen that sensing assembly 26 has a retracted position defined by the contact between diameter step 60-62 and interior housing shoulder 64, and has an extended position defined by the contact between stop ring 66 and packing bushing 70. In addition, it will be seen that sensing assembly 26 may be locked in its extended position by tightening knurled nut 72.

To the end that sensing assembly 26 may be sealed off from the sample fluid in its retracted position, and thereby prepared for cleaning, removal or replacement, a closure device such as a gate valve 74 is included as a part of housing section 24a. In the present embodiment valve 74 is of a conventional type and includes a handwheel 76 which operates in the usual manner to raise and lower a wedge shaped gate element 78 within a wedge shaped channel 80. The opening on the sample end 82 of valve 74 is provided with female threads 84 whereby valve 74 may be fastened to mounting plate 16 by a length of threaded pipe 86. The opposite end 88 of valve 74 is provided with male threads 90 and a tapered interior surface that forms a part of junction J. The latter structures cooperate with nut 25 and a mating tapered surface on the end of housing section 24b to provide a leakproof seal between housing sections 24a and 24b. Since the valve 74 shown in FIG. 1 is conventional in structure and operation, the latter will not be further described herein.

When valve 74 is open, that is, when wedge shaped gate element 78 is in the raised position shown in FIG. 1b, the interior of valve 74 forms a part of chamber 28 and provides an unobstructed opening for the retraction of sensing assembly 26 therethrough. Once assembly 26 assumes its fully retracted position, however, valve 74 may be closed, causing gate element 78 to fit tightly against the walls of channel 80. Under this condition, valve 74 effectively divides chamber 28 into two parts each of which is sealed off from the other. The first of these parts, i.e., the region between member 78 and mounting plate 16 remains open to sample region 12. The second of these parts, i.e., the region between member 78 and sliding seal 71 is sealed off both from sample region 12 and from the atmosphere. The latter part of chamber 28 does, however, contain the sample fluid that was trapped therein by the closure of valve 74.

In order that the sample fluid trapped in chamber 28 may be removed prior to the detachment of housing section 24a from housing section 24b at junction J, there is provided a fluid inlet coupling 94 and a fluid outlet coupling 96. Each of these couplings penetrates housing 24, and each has a female thread that is adapted to receive a mating coupling member (not shown) to which is attached a fluid conduit such as a hose. Fluid inlet coupling 94 permits a source of purging fluid (not shown) to be connected to chamber 28 to supply fluid thereto. Similarly, fluid outlet coupling 96 permits a drain (not shown) to be connected to chamber 28 to receive and safely dispose of fluid displaced therefrom. It will be understood that fluid couplings 94 and 96 may be permanently secured to housing 24 in any suitable manner, such as by welding.

The operation of the embodiment of FIG. 1 will now be described. Assuming that sensor 20 is being used in the position shown in FIG. 1, a user will first loosen knurled nut 72 until it becomes disengaged from housing 24. Sensing assembly 26 may then be withdrawn into chamber 28 until diameter step 60-62 contacts housing shoulder 64. Once this is done, valve 74 is tightly closed to seal off assembly 26 from region 12. Thereafter, a flow of purging fluid is established through inlet 94 and outlet 96 to flush the trapped sample fluid from chamber 28.

Once chamber 28 has been purged, nut 25 may be loosened and the second section 24b of housing 24, with sensing assembly 26 still in place, may be detached from first section 24a at junction J. This exposes sensing element 36 for servicing and replacement, as necessary. Optionally, where particularly toxic fluids are involved, it may be desirable to take additional measures to avoid the leakage of even the tiny amounts of sample fluid that may be able to escape through closed valve 74. If this is the case, the open end of housing section 24a at junction J may be closed with a sealing plug that takes the place of removed housing section 24b. This plug should, of course, have a shape suitable for sealing housing section 24a in the same manner as the end of the removed housing section 24b.

Once sensing assembly 26 has been serviced or replaced, the latter may be restored to the position shown in FIG. 1 by simply reversing the above-described removal sequence. The reversed sequence, however, will ordinarily not include the step of purging chamber 28. This is because there is ordinarily no harm in releasing into region 12 the small quantity of air that is trapped in chamber 28 during the reconnection and re-insertion of assembly 26. Naturally, if the introduction of this trapped air into the sample region is objectionable, chamber 28 may be purged of such air through suitable additional fluid couplings such as 94 and 96 prior to the re-opening of valve 74.

While inlet coupling 94 is illustrated as being at the outer end of the top of chamber 28 and outlet coupling 96 is illustrated as being at the inner end of the bottom of chamber 28, it will be understood that these positions are merely illustrative. In practice, these couplings can be located at any convenient position on housing 24. If, for example, the purging fluid is denser than the sample fluid, it may be advisable to introduce the purging fluid at the lowest point in chamber 28 and remove the purged fluid at the highest point in chamber 28. In addition, the number of inlet couplings and outlet couplings may each be greater than one; embodiments of this type will be described more fully presently in connection in FIG. 4.

The embodiment of FIG. 1 is most conveniently used in applications in which the purging fluid flows into and out of chamber 28 through flexible hoses. This is because the flexibility of such hoses allows housing sections 24a and 24b to be separated (after the loosening of nut 25) without having to disconnect the supply and drain of purging fluid from couplings 94 and 96. If the use of such flexible hoses are for any reason not available or not permissible, however, the need for disconnecting couplings 94 and 96 from the source and drain of purging fluid may still be avoided by utilizing the embodiment of the invention shown in FIG. 2.

Figure 2:
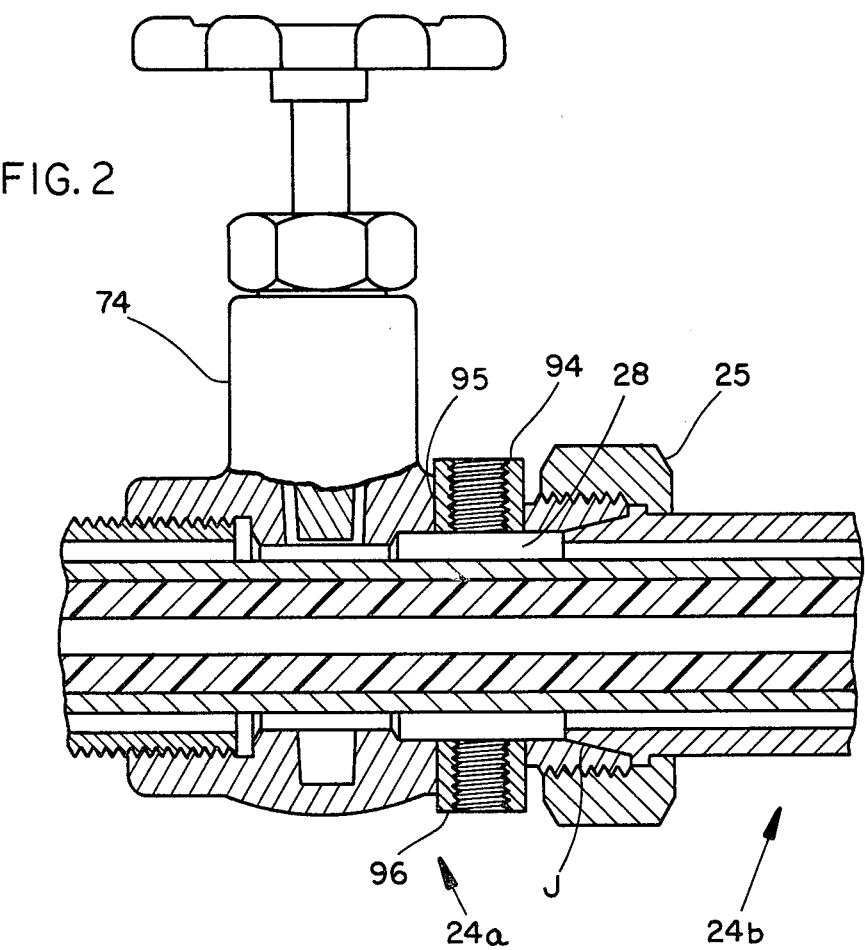
FIG. 2 is a partial cross-sectional view of another embodiment of the invention.

Referring to FIG. 2, there is shown an embodiment of the invention in which the purging fluid inlet and outlet couplings 94 and 96 are located on valve 74 of first housing section 24a, rather than in second housing section 24b. The latter choice of location, however, may require that valve 74 be machined so as to provide a sufficient space 95 for coupling 94 to be solidly seated on the valve housing. The location of couplings 94 and 96 on housing section 24a allows the purging fluid supply and drain conduits to remain attached to housing section 24a as housing section 24b is removed for the servicing of assembly 26. Because chamber 28 can be purged by fluid introduced into housing section 24a as well as by fluid introduced into housing section 24b, it will be seen that the present invention does not require particular locations for the purging fluid couplings. One possible exception occurs where particularly hazardous fluids are used with the previously mentioned sealing plug for junction J. In such cases, the purge fluid couplings are preferably located on housing section 24a so that the part of chamber 28 that is closed by the plug may be purged a second time prior to its removal and replacement by housing section 24b. In view of the functional similarity between the embodiments of FIGS. 1 and 2, and the embodiment of FIG. 2 will not be further described herein.

In many applications the use of a sliding seal such as that provided by sealing ring 71 is unable to totally prevent the escape of sample fluid. Seal 71 may, for example, loosen as a result of wear and/or chemical deterioration and allow appreciable quantities of the sample fluid to escape without being detected. In accordance with one feature of the present invention, this problem may be entirely eliminated by using the embodiment of the invention illustrated in FIG. 3.

Figure 3:
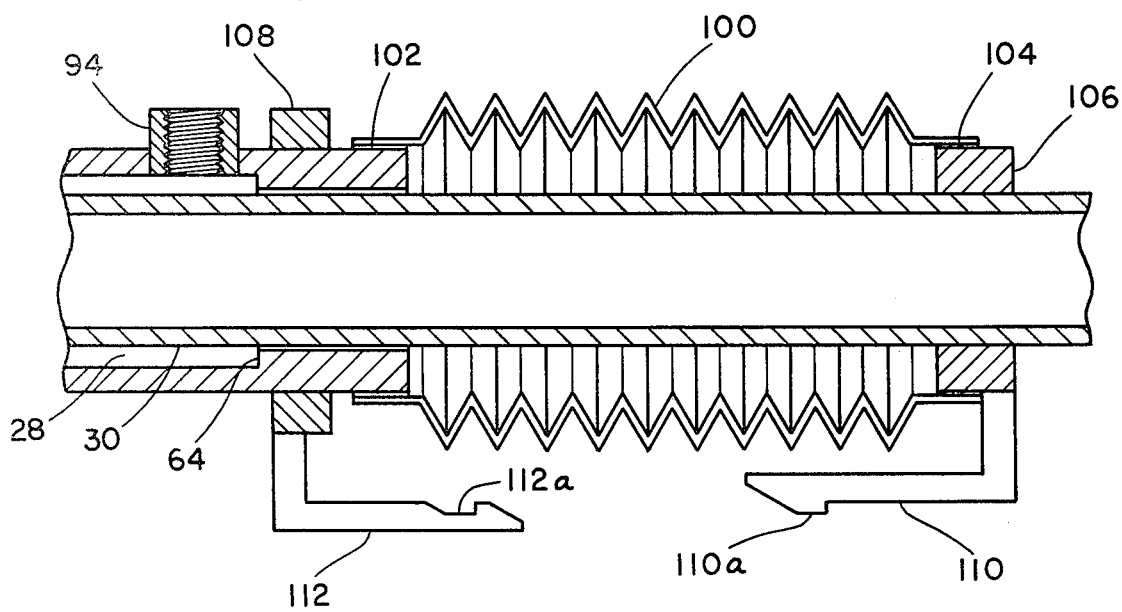
FIG. 3 is a partial cross-sectional view of an embodiment of the invention that is provided with a non-sliding seal.

Referring to FIG. 3, there is shown a partial cross-sectional view of the end portion of housing section 24b, corresponding parts in all figures being similarly numbered. The embodiment of FIG. 3 differs from that of FIGS. 1 and 2 in that in FIG. 3 seal 71, packing bushing 70, stop ring 66 and knurled nut 72 are eliminated. In their place the embodiment of FIG. 3 includes a generally tubular flexible enclosure 100 which can be longitudinally extended and compressed in the manner of an accordion or bellows. One end of enclosure 100 is connected to the end of housing section 24b. If enclosure 100 is made of a weldable metal such as stainless steel, this connection may be made by means of a leakproof circular weld that extends around the circumference of housing 24. Similarly, the other end of enclosure 100 is preferably connected in a like manner to a generally annular spacer 106 which is, in turn, welded to mounting element 30. If enclosure 100 is made of a non-metallic substance such as rubber, these connections may be made by suitable hose clamps of any suitable type.

With the embodiment of FIG. 3 the leakproof connections between the ends of enclosure 100, housing 24 and mounting element 30, assure that no path is provided for the escape of sample fluid for any of the possible positions of sensing assembly 26 within housing 24. As a result, it will be seen that the embodiment of FIG. 3 provides the desired sealing action without the use of a sliding contact between the relatively movable members 24 and 30. In this manner, the possibility of leaks occurring as a result of the wearing and consequent loosening of a sliding seal is avoided. It will be understood, however, that the use of the flexible enclosure of FIG. 3 does not preclude the use of a sliding seal or bushing of the type shown in FIG. 1, if the presence of the latter are desirable for other purposes, such as guiding the movement of assembly 26 within housing 24.

Because of the absence from the embodiment of FIG. 3 of knurled nut 72, the embodiment of FIG. 3 will not, without additional structure, lock mounting assembly 26 in its extended position. The desired locking action may, however, be provided in the embodiment of FIG. 3 by adding thereto any suitable locking mechanism. One such locking mechanism, for example, includes a locking arm 110 extending from spacer 106 and a cooperating locking arm 112 extending from an annular mounting member 108. By providing spacer 106 and mounting member 108 with arms 110 and 112, respectively, assembly 26 may be locked in its extended position as locking projection 110a snaps into place in a locking groove 112a. The unlocking of assembly 26 is accomplished by bending arm 110 until projection 110a is released from groove 112a. Many other locking mechanisms will be apparent to those skilled in the art.

In applications in which sensing element 36 is used in a sample environment in which dirt particles or contaminants tend to adhere thereto, the present invention contemplates an improved arrangement whereby sensing element 36 may be cleaned before (or even without) removing it from housing 24. If, for example, the rapid accumulation of soot or other deposits on element 36 makes it necessary to clean element 36 relatively frequently, it may be desirable to perform the necessary cleaning without going through all of the steps necessary to remove housing section 24b from housing section 24a. One embodiment of the invention that is adapted to clean sensing element 36 without opening housing 24 is illustrated in FIG. 4.

Figure 4:
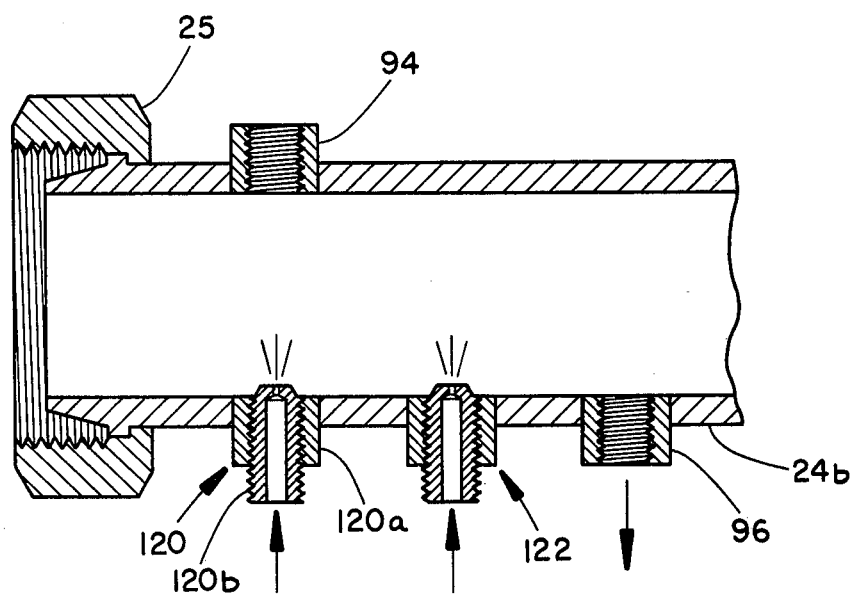
FIG. 4 is a partial cross-sectional view of an embodiment of the present invention that is provided with an arrangement for spraying a purging or cleaning fluid against the sensing element.

Referring to FIG. 4, there is shown a partial cross-sectional view of one end of housing section 24b. The embodiment of FIG. 4 differs from that of FIG. 1 primarily in that the embodiment of FIG. 4 includes additional fluid inlets 120 and 122 through which a suitable cleaning fluid may be introduced and directed against those portions of sensing element 36 which are most in need of cleaning. Fluid inlet 20, for example, may be positioned so that it directs a spray of fluid across the opening of passage 48 of sensing element 36, while fluid inlet 122 is positioned to direct a spray of fluid into hole 50 in the side of sensing element 36. When fluid inlets of this type are used to clean specific parts of element 36, the number and position of these fluid inlets will naturally depend on the type of sensing element being used. It will, therefore, be understood that all numbers, positions and orientations of inlets and outlets are within the contemplation of the present invention.

In the embodiment of FIG. 4, inlets 120 and 122 may each include an outer support element such as 120a which has the same structure as elements 94 and 96 in FIGS. 1–3, and an inner flow directing element 120b that is threaded to fit into outer element 120a. Preferably, flow directing element 120b is provided with an orifice 120c which forms the cleaning fluid into a jet or spray having the desired spread and flow rate, in a manner well known in the art. In this way, inlets 120 and 122 provide a flow of cleaning fluid in both the form and direction necessary to provide the desired cleaning action. It will be understood that flow directing elements such as 120b may also be used with purging fluid inlet 94 to form the purging fluid into a suitable jet or spray.

Depending upon the intended application, the cleaning fluid introduced through inlets 120 and 122 may be either in addition to or in place of the purging fluid introduced through previously described couplings 94 and 96. If, for example, it is desirable to purge chamber 28 with a gas but to clean element 36 with a liquid, the structure shown in FIG. 4 may be used. More particularly, the desired purging action may be accomplished by means of couplings 94 and 96, in the manner previously described. Thereafter, when the cleaning operation is to be performed, a suitable cleaning fluid may be introduced through inlets 120 and 122 and removed through outlet 96, or a separate additional outlet provided for that purpose.

On the other hand, if a single fluid can be used for both purging and cleaning, these operations may be performed simultaneously. In such a case, coupling 94 might be eliminated and both operations performed by introducing the fluid, either a liquid or a gas, through inlets 120 and 122 and removing the same through outlet 96. These and other variations are possible since the cleaning and purging operations are ordinarily overlapping rather than mutually exclusive. This is because the purging operation provides some degree of cleaning action and because the cleaning operation necessarily removes trapped sample fluid from within housing 24. Thus, the terms purging and cleaning are largely interchangeable, the choice of one over the other being a reflection of the end result being emphasized.

Figure 5:
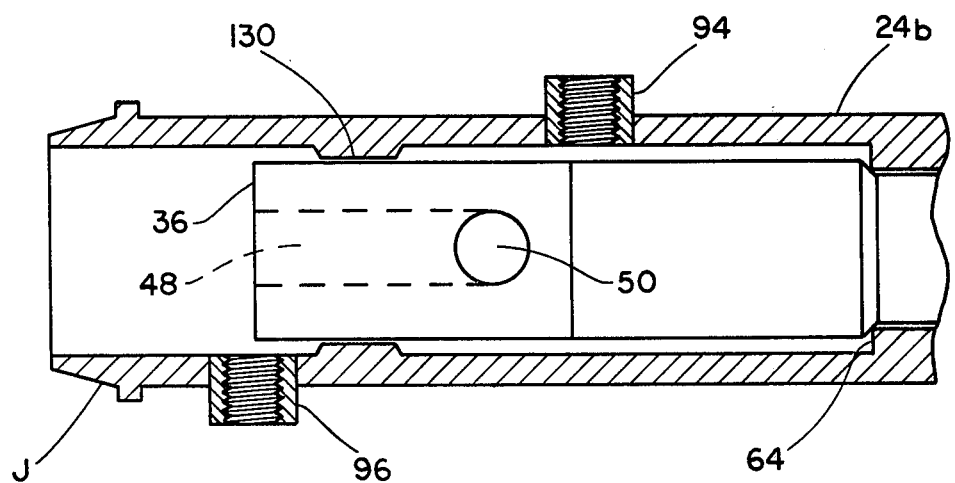
FIGS. 5, 6a and 6b are partial cross-sectional views of embodiments of the present invention that are provided with alternative arrangements for directing purging and/or cleaning fluid flow over the sensing element.

The cleaning and purging operations may also be accomplished simultaneously by the use of the embodiment of the invention shown in in FIG. 5. The part of sensor 20 that is shown in FIG. 5 is the same as the corresponding part of the sensor shown in FIG. 1 except that the embodiment of FIG. 5 includes a generally annular fluid flow directing projection or constriction 130 between couplings 94 and 96. By effectively preventing fluid from flowing through the part of chamber 28 that is obstructed by constriction 130, constriction 130 forces fluid to flow through an alternative path between couplings 94 and 96. In the presence of a sensing element of the type shown in FIG. 1, for example, the only such alternative path is the internal opening defined by passage 48 and hole 50. As a result, it will be seen that the embodiment of FIG. 5 establishes within chamber 28 a fluid flow pattern suitable for rinsing sensing element 36 clean of accumulated dirt at the same time that chamber 28 is purged of the sample fluid. Naturally, if the composition of the purging fluid must be different from that of the cleaning fluid, the embodiment of FIG. 5 may be provided with separate sets of purging and cleaning fluid couplings.

Figure 6A:
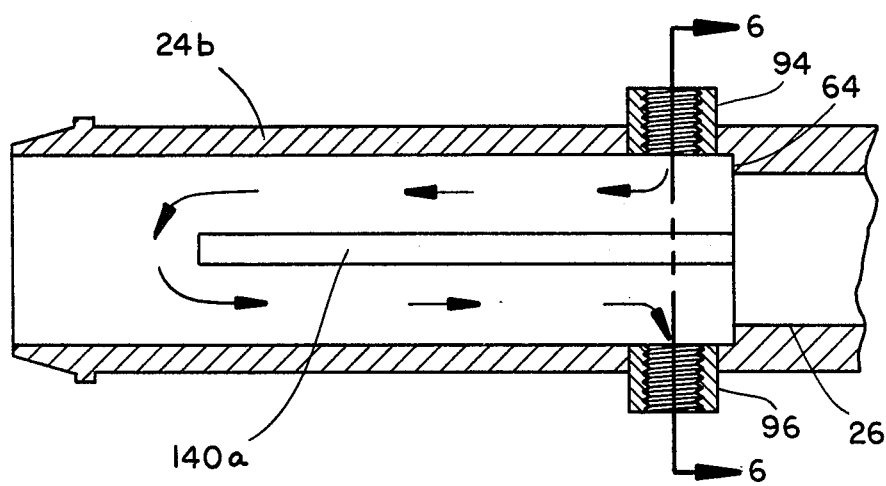
Figure 6B:
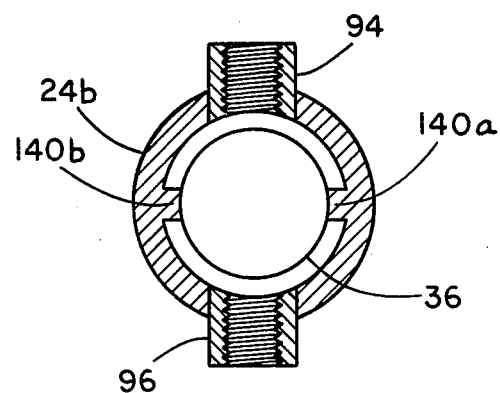

The use of a fluid flow directing constriction to combine the desired purging action with the desired cleaning action is not confined to sensing elements such as 36 that have internal fluid flow passages. Referring to FIGS. 6a and 6b, for example, there are shown two cross-sectional views of still another embodiment of the invention. The cross sectional view shown in FIG. 6b is taken through the line 6—6 of FIG. 6a, certain background detail being omitted for the sake of clarity. The embodiment of FIGS. 6a and 6b differs from that of FIG. 5 in that the flow directing arrangement of FIGS. 6a and 6b is disposed longitudinally rather than radially as in FIG. 5. In FIGS. 6a and 6b, the flow directing arrangement includes longitudinal strips 140a and 140b which extend substantially from the inner wall of housing section 24b to the outer wall of sensing element 36. It will be understood that strips 140a and 140b may extend over any desired portion of the entire length of sensing element 36 or even beyond, toward junction J.

While it is preferred that longitudinal strips 140a and 140b be attached to the inside of housing section 24b, this location is not essential to the practice of the present invention. It may, for example, be desirable for longitudinal strips 140a and 140b to be attached to the sides of sensing element 36. If the latter point of attachment is used, however, guide pins or slots may be necessary to assure that longitudinal strips 140a and 140b do not rotate so as to block the inlet 94 and outlet 96 during the retraction of assembly 26.

In operation, the embodiment of FIGS. 6a and 6b directs the inflow of fluid from inlet 94 so that it flows over substantially the entire external surface of sensing element 36 before reaching outlet 96. This occurs because constrictions 140a and 140b effectively partition chamber 28 into moving semicylindrical shells of fluid which sweep over the surface of sensing element 36 in the direction indicated by the arrows. It will be understood that the embodiment of FIGS. 6a and 6b may also be provided with separate sets of fluid couplings for cleaning fluid and for purging fluid, as described in connection with FIG. 4.

In view of the foregoing, it will be seen that the present invention not only provides an improved mechanism for removing and replacing a sensing element without the escape of sample fluid, but also provides a new sealing structure whereby the deterioration and leakage associated with sliding seals is avoided and, in addition, provides a fluid flow directing arrangement whereby a sensing element may be cleaned as well as purged, without disassembly of the sensor mechanism.

While the foregoing invention has been described in relation to a number of specific embodiments, it will be understood that the true scope of the present invention should be determined only with reference to the following claims.

What we claim is:

1. An improved sensor mechanism for performing measurements on sample fluids that are not to be allowed to escape into the environment, said sensor mechanism comprising, in combination,
   (a) a housing having first and second sections;
   (b) a retractable sensing assembly within said housing, said sensing assembly having an extended position in which the sensing assembly extends into or through the first housing section, and a retracted position in which the sensing assembly occupies the second housing section;
   (c) a closure device in said first housing section, said closure device having an open state in which an open path is provided for the movement of the sensing assembly between the first and second housing sections, and having a closed state in which the second housing section is sealed off from the source of sample fluid;

(d) an inlet and an outlet in said housing whereby fluids trapped within the housing by the closure of the closure device may be removed for safe disposal;

(e) fastening means for fastening and unfastening the first and second sections of the housing; and (f) a seal between the sensing assembly and the housing for preventing the leakage of fluid for all positions of the sensing assembly.

2. A sensor mechanism as set forth in claim 1 in which said seal provides a sliding contact between the sensing assembly and the housing.

3. A sensor mechanism as set forth in claim 1 in which said seal includes an expandable enclosure having an opening at each end thereof, means for attaching one end of the enclosure to the housing and means for attaching the other end of the enclosure to the sensing assembly.

4. A sensor mechanism as set forth in claim 3 in which said expandable enclosure comprises an accordion-like structure.

5. A sensor mechanism as set forth in claim 1 in which said inlet and outlet are fluid couplings located on the first housing section.

6. A sensor mechanism as set forth in claim 1 in which said inlet and outlet are fluid couplings located on the second housing section.

7. A sensor mechanism as set forth in claim 1 including a plug for sealng the first housing section after the removal of the second housing section.

8. A sensor mechanism as set forth in claim 1 in which said inlet includes means for directing a flow of a purging fluid against at least one selected portion of the sensing assembly to clean the surface thereof.

9. A sensor mechanism as set forth in claim 8 in which said flow directing means comprises a nozzle.

10. A sensor mechanism as set forth in claim 1 in which said inlet and said outlet comprise couplings for respective connection to a source of and drain for a purging fluid.

11. A sensor mechanism as set forth in claim 10 including a cleaning fluid inlet and a cleaning fluid outlet for respective connection to a source of and drain for a cleaning fluid.

12. A sensor mechanism as set forth in claim 1 in which either said sensing assembly or said housing includes flow directing means for directing the flow of a fluid entering said inlet and exiting said outlet against the sensing assembly.

13. A sensor mechanism as set forth in claim 12 in which said flow directing means is a circumferential constriction between said inlet and said outlet.

14. A sensor mechanism as set forth in claim 12 in which said flow directing means is a longitudinal constriction.

15. An improved sensor mechanism having a sensing assembly for performing measurements in a sample environment that must be isolated from another environment, said sensor mechanism comprising, in combination:

(a) a housing having first and second sections;

(b) a retractable sensing assembly including a sensing element and a mounting element, said assembly having an extended position in which the sensing element extends at least into the first housing section and a retracted position in which the sensing element is substantially confined to the second housing section;

(c) a closure device for sealing the second housing section off from the sample environment when the sensing element is in its retracted position;

(d) a seal between the mounting element and the housing;

(e) at least one inlet in the housing for introducing a flow of fluid into the vicinity of the sensing element when the sensing assembly is in its retracted position and the closure device has sealed off the second housing section; and (f) at least one outlet in the housing for the removal of said fluid.

16. A sensor mechanism as set forth in claim 15 in which said seal is a seal with which the mounting element has a sliding contact.

17. A sensor mechanism as set forth in claim 15 in which said seal comprises an accordion-like enclosure having a first end fastened to said housing and a second end fastened to said mounting element.

18. A sensor mechanism as set forth in claim 15, 16 or 17 in which a purging fluid is introduced through one or more of said at least one inlet in the form of a spray.

19. A sensor mechanism as set forth in claim 15, 16 or 17 in which a cleaning fluid is introduced through one or more of said at least one inlet in the form of a spray.

20. A sensor mechanism as set forth in claim 15 further comprising an inlet for connection to a source of a purging fluid and an inlet for connection to a source of a cleaning fluid.

21. A sensor mechanism as set forth in claim 15 in which the space between said housing and said sensing assembly includes a constriction for directing the flow of a cleaning and/or purging fluid against the sensing element as it flows from said at least one inlet to said outlet.

22. A sensor mechanism as set forth in claim 21 in which said constriction is generally perpendicular to the axis of the housing.

23. A sensor mechanism as set forth in claim 21 in which said constriction is generally parallel to the axis of the housing.

* * * * *